United States Patent [19]

Byrne et al.

[11] 4,004,882
[45] Jan. 25, 1977

[54] GAS ANALYSIS DILUTER

[75] Inventors: James Donald Byrne, San Diego; Paul Arthur Griffith, Fallbrook, both of Calif.

[73] Assignee: Monitor Labs, Incorporated, San Diego, Calif.

[22] Filed: Aug. 14, 1975

[21] Appl. No.: 604,879

[52] U.S. Cl. .................... 23/254 R; 73/421.5 R
[51] Int. Cl.$^2$ .......................... G01N 1/22
[58] Field of Search ......... 23/254 R, 254 E, 255 R, 23/255 E, 232 R, 232 E; 73/421.5 R, 422 R, 421.5 A

[56] References Cited
UNITED STATES PATENTS

| | | | |
|---|---|---|---|
| 3,367,850 | 2/1968 | Johnson | 23/254 R |
| 3,545,931 | 12/1970 | McKinley, Jr. | 23/254 R |

*Primary Examiner*—R.E. Serwin
*Attorney, Agent, or Firm*—Brown & Martin

[57] ABSTRACT

A mass exchange device and system that employs a semi-permeable diffusion barrier in the nature of a tubular membrane. A sample gas stream conduit is concentric with the tubular membrane, and the transport gas stream flows within the tubular membrane in a direction opposite to the flow of transport gas stream. Certain molecular species in the sample gas migrate across the tubular membrane and mix with the transport gas for passage to an analyzer. The conduit and tubular membranes are incorporated within a heat exchange cartridge and a heater and temperature controller maintain a desired temperature control of the system. Dual stream dilutions may be accomplished by sampling an exhaust gas prior to cleansing by a gas scrubber and also sampling the gas after cleansing. Both the upstream and downstream sample gases are diluted in a common heat exchange cartridge and passed to an analyzer.

9 Claims, 7 Drawing Figures

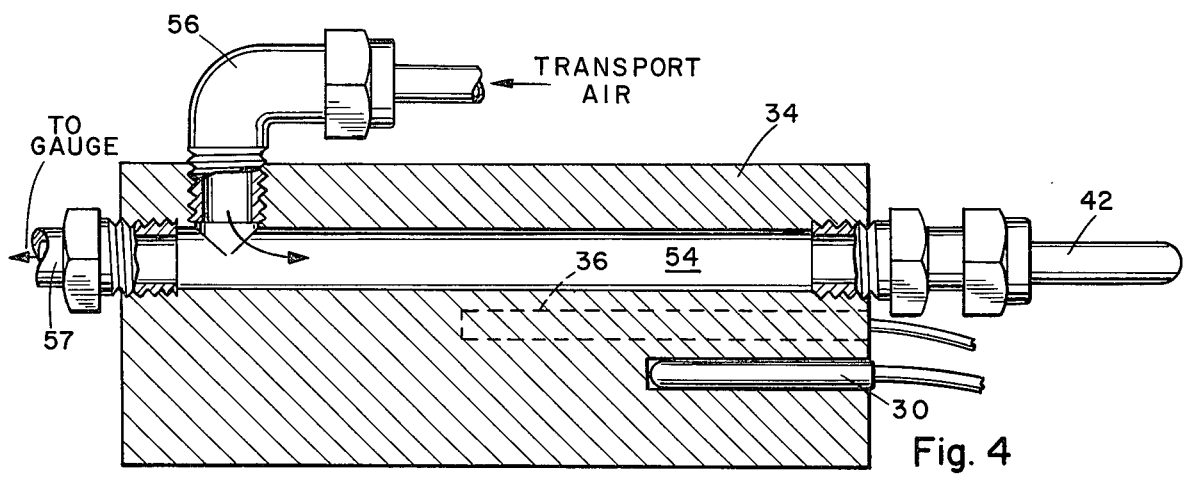
Fig. 4
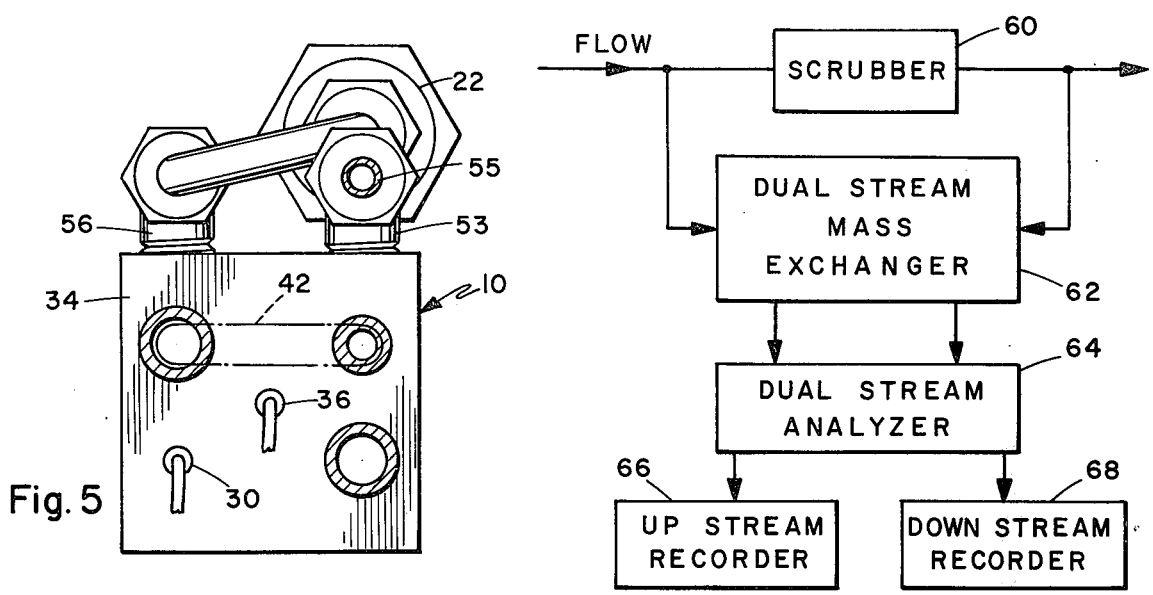
Fig. 5
Fig. 7
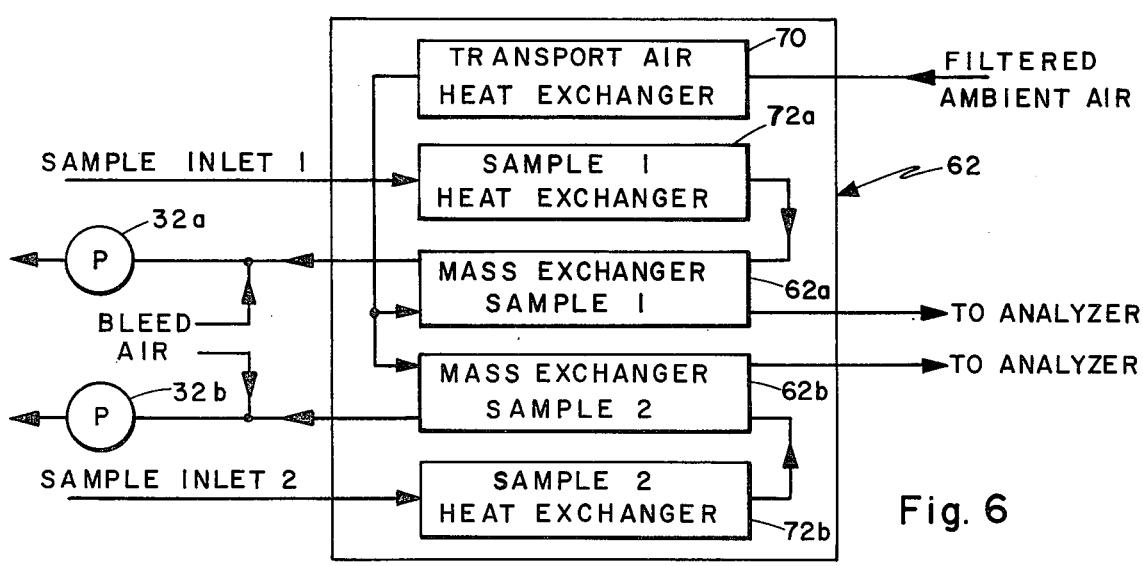
Fig. 6

GAS ANALYSIS DILUTER

BACKGROUND OF THE INVENTION

The present invention relates to a gas analysis diluter for use with analyzers such as those employed in association with industrial exhaust stacks.

Environmental considerations necessitate the cleaning of exhaust gases which are the by-products of many industrial systems. To determine the effectiveness of the cleansing system, gas analyzers are often incorporated to monitor the efficiency of the gas scrubber and other pollution control equipment. These analyzers are usually of the infrared, chemiluminescent, flame ionization, or flame photometric type wherein the samples are extracted from the source and transported to the analyzer continuously or by a batch process.

The proper functioning of most analyzers necessitates that a suitable interface exist between the analyzer and the source of molecules under analysis. Accordingly, it is necessary to condition the sample to make it acceptable to the analyzer. This is analogous to sample preparation requirements for standard wet chemical or other laboratory techniques. For example, where a flame type detector utilizes the burning of hydrogen and oxygen, the flame cannot be sustained by a sample which does not contain a sufficient concentration of oxygen. Therefore, a flame ionization detector cannot analyze a hydrocarbon stream directly without first supplying air to the analyzer. In most cases a controlled sample stream is mixed with a desired amount of air or oxygen prior to combustion in the detector. The admixture of the sample, and what may be called the transport gases, represents the interfacing of the two gas streams so that the resultant sample is properly conditioned to make it acceptable to the analyzer.

The conditioning of the sample gas entails the removal of particulate matter to very low concentration levels. It is also necessary that water vapor be removed so that the concentration levels thereof are low enough to prevent condensation in the analyzer or the sample transport device, Similarly, the acid vapor or mist concentration must be reduced so as to avoid condensation thereof in the analyzer or the sample transport device. Along with these requirements, there is the necessity of preventing condensation of organic liquids arising from boiler combustion processes.

In present art analyzers the presence of carbon dioxide in the stack exhaust seriously interfers with the operation of chemiluminescent type analyzers. High level concentrations of carbon dioxide can reduce the signal produced by a chemiluminescent reaction for equal concentrations of a particular molecular species from the signal level produced when carbon dioxide is absent from the sample. This negative carbon dioxide interference is commonly called quenching. A common present art technique designed to interface a chemiluminescent analyzer with a source stream involves dilution of the sample by purely pneumatic means. A small sample stream is mixed with a very large stream of clean air or transport gas under controlled conditions. This has the effect of diluting the concentration of all molecular species in the sample stream proportionally to the ratio of the size of the transport gas stream and the sample gas stream. It has been found that there are serious side effects to such a system. The sample is basically unconditioned and this introduces all constituents, in a diluted form, in the exhaust gas stream which include particulates and acid mist into the instrument via the diluter. Such contaminants may plug the equipment or otherwise damage the equipment and thereby introduce faulty readings. The dilution factors utilized are generally insufficient to dilute the sample so as to remove all the harmful particulates or acid mist to insignificant levels. The exposure to contaminants necessitates daily maintenance of the analyzers to keep them in effective operating condition. These systems are not amendable to finer filtration since in practice more extensive filtration interferes with the operation of the system.

It has been found that dilution of sample by means of a diffusion device is more reliable in that the analyzer system is permitted to function at optimum efficiency. The invention recognizes the voids in the prior art for effective sample dilution so that the readings of the analyzer are representative of the exact condition or makeup of the exhaust gas stream.

SUMMARY OF THE INVENTION

It is an object of the invention to provide a new and improved gas analysis diluter which effectively dilutes a sample gas stream to permit an analyzer to operate at optimum efficiency.

Another object of the invention is the provision of a new and improved gas analysis diluter which is effective to remove particulates and dilute to relatively low concentration levels of water and acid vapors from the sample gas stream which are deleterious to the functioning of the analyzer.

Another object of the invention is the provision of a new and improved gas analysis diluter which permits certain molecular species to pass into the analyzer at higher rates than other molecular species.

A further object of the invention is the provision of a new and improved gas analysis diluter which is temperature controlled and designed to function independently of the exhaust gas temperature.

Still another object of the invention is the provision of a new and improved gas analysis diluter that monitors the exhaust gas condition before and after scrubbing.

Yet another object of the invention is the provision of a new and improved gas analysis diluter effective for use with various diffusion rates.

Yet another object of the invention is the provision of a new and improved gas analysis diluter that is compact, durable and efficiently designed.

Yet another object of the invention is the provision of a new and improved gas analysis diluter which does not alter the chemical form of the molecular species undergoing analysis.

In accordance with the above designs, the gas analysis diluter includes a conduit formed in a heat exchange cartridge. A tubular membrane is concentric with and enclosed within the conduit. The conduit receives a heated and filtered sample gas. A transport gas stream made up of ambient air is filtered and some of its impurities oxidized and then refiltered, and is then transmitted into the tubular membrane in a direction opposite to the flow direction of the sample gas.

The tubular membrane functions as a diffusion barrier and is fabricated from a permeable material which is permeable gas molecular species. Some of the sample gas molecules migrate across the membrane and mix with the transport gas which is then transported to an analyzer for appropriate analysis. The sample gas which does not migrate across the diffusion membrane is exhausted by means of a pump. A heater is situated in the heat exchange cartridge and appropriately heats that cartridge. A temperature controller regulates the heater and this controls the cartridge temperature level with 0.1° C. A temperature sensing probe is in thermodynamic relation with the heat exchange cartridge and continuously senses the temperature thereof for appropriate control adjustment.

A dual stream diluter may sample exhaust gas upstream and downstream of a gas scrubber. The upstream and downstream samples are diluted by means of the dilution barriers in a common heat exchange cartridge. The individual diluted streams are then analyzed and recorded for comparison.

The above and other aspects of the invention will be apparent as the description continues and when read in conjunction with the appended drawings.

BRIEF DESCRIPTION OF THE DRAWINGS

FIG. 4 is an enlarged sectional view taken along the line 4—4 of FIG. 2.

FIG. 5 is a sectional view taken along the view 5—5 of FIG. 3.

FIG. 6 is a diagram of dual stream mass exchanger unit.

FIG. 7 is a diagram showing a typical use of the dual stream unit.

DETAILED DESCRIPTION OF THE DRAWINGS

Figure 1:
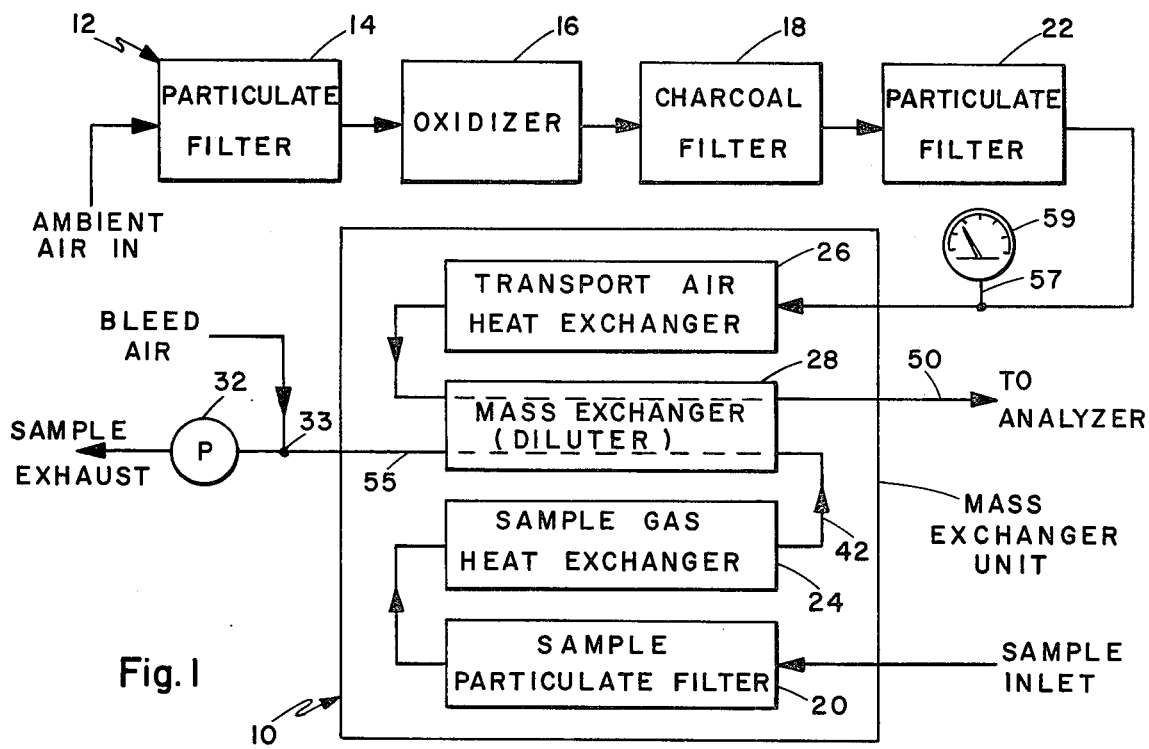
FIG. 1 is a diagram of the apparatus utilizing the mass exchange unit.

Referring to the drawings wherein like numerals indicate like elements in the various figures, the gas analysis diluter generally referred to by the numeral 10 requires a filtering stage characterized by the multicomponent filtering means 12. The filtering means 12 conditions the transport air prior to entering the diluter 10, by reducing particulate material concentrations to very low levels. The filtering means 12 comprises a first particulate filter means 14 designated in block form in FIG. 1. The transport air is then passed into an oxidizer 16. The oxidizer produces ozone which reacts with gases like nitric oxide that may be present in the transport air stream to produce nitrogen dioxide. The need for oxidizer 16 will depend upon the application of the invention. There may be some applications where oxidizer 16 is not needed. Downstream from the oxidizer 16 is an activated charcoal filter 18 which filters out the nitrogen dioxide generated in the oxidizer 16. Other impurities such as sulfur dioxide and hydrogen sulfide are also removed by activated charcoal filter 18. Further downstream from the charcoal filter 18 is a second particulate filter 22 which further filters the transport or ambient air stream to remove any particulates which may have been generated from the decomposition of the charcoal filter 18.

The sample gas to be analyzed is introduced into a sample particulate filter 20 to remove particulates that would be harmful to the operation of the analyzer. At this point, the conditioned transport air stream and the sample gas stream are passed into respective heat exchangers 26 and 24 which adjust the temperatures of the gases for efficient and predictable dilution in a mass exchanger or diluter 28. The system is provided with a temperature sensing device 30 which continuously senses the on-going temperature of the system for control of the settings of the heat exchangers 24 and 26, so as to continuously condition the transport and sample gas stream temperatures for effective dilution. A part of the sample gas stream then migrates across diffusion barrier means in the diluter 28. The molecular species of the sample gas that is permitted to migrate in the diluter mixes with the transport gas which is then directed to an analyzer for an assay of its contents. The sample gas that does not migrate past the diluter is exhausted from the system by means of a pump 32 which pulls in bleed air at 33. The pump 32 draws in substantially more bleed air than it does sample gas. The bleed air eliminates the possibility of rupturing the diffusion barrier means should the diluter become clogged or plugged. Accordingly, in the event of plugging, the pump 32 simply draws in bleed air rather than causing a harmful pressure differential in the diluter.

The material utilized as a dilution barrier must have a relatively high mass conduction with respect to the molecular species that is to migrate past the barrier. Gas molecules on one side of the diffusion barrier dissolve into that barrier material at the surface thereof. The molecules then migrate through the material via a diffusion process to the opposite side and undissolve thereat. In most circumstances, any material may be used as a diffusion barrier so long as it has a sufficient mass conductance to the molecular species under analysis. In practice, it has been found that materials such as Teflon, silicone rubber, polyethylene, and other organic materials possess the proper mass conductance and in addition have the appropriate temperature characteristics for the system to function properly. Teflon has been found to be particularly effective for analysis. Other geometrical configurations may be employed as a diffusion barrier. The embodiment disclosed has particular advantages with regard to replaceability and durability. The mass exchange rates across the diffusion barrier means are dependent only upon the temperature of the sample and transport gas streams and the mass conductance of the diffusion barrier with respect to the particular molecular species.

Figure 2:
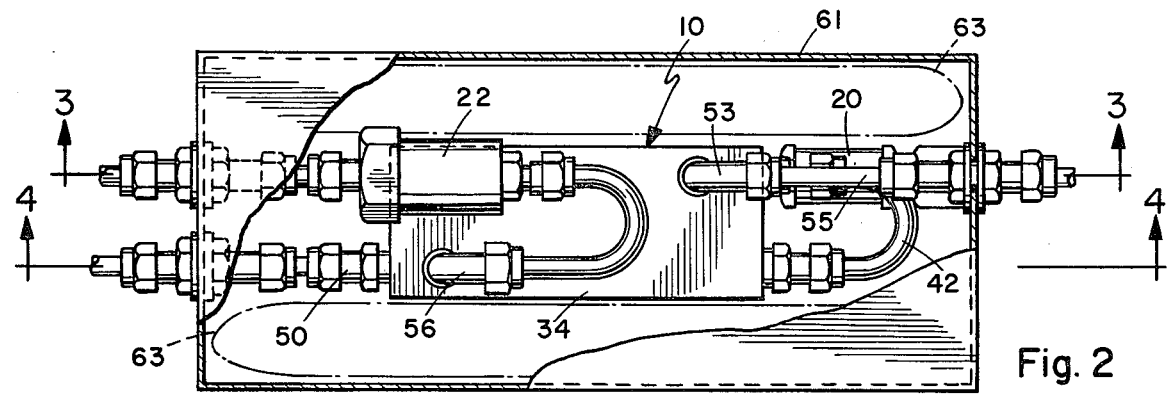
FIG. 2 is a top plan view, partially cut away, of the mass exchanger unit.
Figure 3:
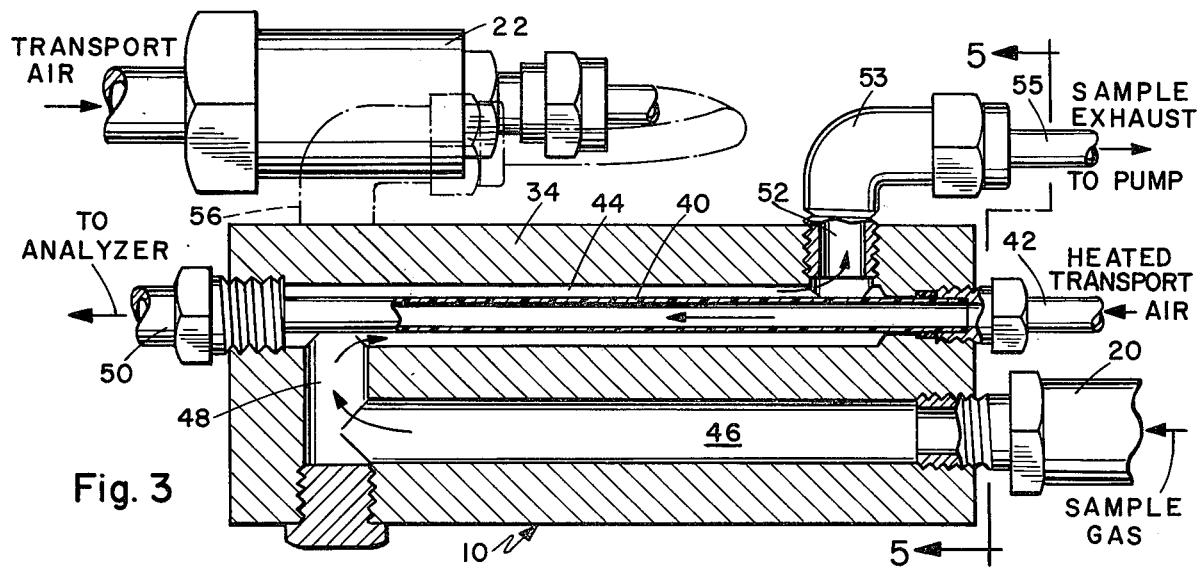
FIG. 3 is an enlarged sectional view taken along the line 3—3 of FIG. 2.

The heat exchangers 24 and 26 of FIG. 1 may be embodied in a solid metallic parallelpiped cartridge 34 of FIG. 2 which must be highly conductive to heat. It has been found that stainless steel, aluminum or copper are materials which adequately satisfy the system operating conditions. All surfaces which contact the sample gas must be made inert. When using aluminum or copper, it is essential to coat completely the interior surfaces with materials similar to Teflon. The coating must be relatively uniform and must be complete so as not to expose any bare metal surface to the gases entering the cartridge. The heater 36 extends lengthwise into the cartridge 34 and the on-going temperature status of the cartridge 34 is sensed by the temperature probe 30. It is necessary to precisely control the temperature of the diluter to establish the dilution that is desired and to maintain it at a constant level. The temperature sensing device 30, therefore, is a proportional type temperature controller. For example, operation of the apparatus at 200° Centigrade with ±0.1° C control will yield approximately ±1% stability for $SO_2$ permeation through Teflon.

By packaging the heat exchangers 24 and 26 and the diluter 28 in a single compact cartridge, a highly sensitive temperature controller may be utilized which is able to maintain temperature control within the narrow limits required for the desired permeation. This advantage is more apparent when utilized in a dual sampling system where the temperature is carefully controlled in a unit that occupies a minimum of space and is less costly than separately packaged units.

The diluter 28 is of a design to produce counter-current concentric flow of the sample and transport gases. Accordingly, the diluter is constructed of a tubular membrane barrier 40 that is situated within the exchange cartridge 34 and which extends essentially the entire length of that cartridge. The heated transport air is transmitted into the tubular membrane barrier 40 via the conduit 42. A part of the sample gas migrates across the tubular membrane 40 and dissolves into the transport air within the tubular membrane 40 which is formed concentrically within the conduit 44. The sample gas stream is directed into the cartridge 34 through the second particulate filter 20 and it enters the conduit 46 from which it passes into the conduit 48 that changes its direction by 90°. The conduit 48 is disposed perpendicular to the conduit 44 and the sample gas stream is then turned a full 180° from its entrance direction and it flows counter-currently to the direction of the flow of the transport air stream. That part of the sample air stream which does not migrate past the diffusion barrier is exhausted through the conduit 52, elbow 53 and conduit 55 by means of the pump 32 as has been previously described. That part of the sample that migrates through the tubular membrane 40 mixes with the transport gas and follows the direction on the flow of the transport gas and enters into conduit 50 which directs it to an analyzer for analysis. The transport air stream is transported into the conduit 54 by means of an elbow 56. The conduit 54 runs substantially the length of the cartridge 34 and is in heat transfer relation therewith so as to heat the sample gas stream to the desired temperature. The transport air is then passed through the conduit 42 and into the tubular membrane 40. An additional outlet 57 from conduit 54 leads to a pressure gauge 59, which indicates the pressure of the incoming transport air stream.

To maintain the heat balance, the diluter 10 and some of its associated apparatus are preferably enclosed in a housing 61, and any spaces are filled with thermal insulation material 63, indicated in broken line in FIG. 2.

The rate of diffusion through the tubular membrane is described approximately by the following equation:

$$Qs = 2 \pi L\, Pm\, Ps\, /\, \ln(ro/ri)$$

where
$Qs$ = sample transport rate
$L$ = inner tube length
$Pm$ = inner tube material permeability coefficient for sample molecules
$Ps$ = partial pressure of sample in sample gas
$ro$ = inner tube outside radius
$ri$ = inner tube inside radius.

The percentage of sample gas that mixes with the transport gas is defined by the equation:

$$Cst = [Qs/Qt]\, 10^6$$

where
$Cst$ = sample concentration in transport gas
$Qt$ = transport gas flow rate The preceding equations may be combined as follows:

$$Cst = \left[\frac{2\pi L\, Pm\, Ps}{Qt\, \ln(ro/ri)}\right] 10^6$$

To obtain a relationship between $Cst$ and the sample concentration of the sample gas, the expression for $Ps$ in terms of the sample concentration must be utilized $$Ps = (Cs\, Pt)\, 10^6$$

where
$Cs$ = sample concentration of sample gas
$Pt$ = sample as total pressure
By substitution:

$$Cst = \left[\frac{2\pi L\, Pm\, Pt}{Qt\, \ln(ro/ri)}\right] Cs$$

This equation shows that the sample is diluted by the factor:

$$\epsilon = \frac{Qt\, \ln(ro/ri)}{2\pi L\, Pm\, Pt}$$

Therefore $Cs = \epsilon\, Cst$

An examination of the equation shows that the sample diffusion rate $\epsilon$ is independent of sample flow rate providing the tubular barrier membrane 40 temperature is controlled and pressure losses are not excessive. The signal produced by the analyzer is proportional to the sample concentration in the transport gas stream multiplied by the dilution factor $\epsilon$.

The diluter 10 may be utilized in conjunction with an exhaust stack that cleans the exhaust gases such as conventional scrubber 60. In many systems, it is necessary to determine the efficiency of the scrubber and this calls for a comparison between the concentration of the molecular specie in the sample gas prior to the scrubbing step as against the molecular specie concentration of the cleansed gas. To this end, a dual stream mass exchanger 62 is utilized in conjunction with a scrubber 60. One branch 62a samples the sample gas prior to entering the scrubber 60, and the other branch 62b samples the gas upon emerging from the scrubber 60. The dual stream mass exchanger or diluter 62 then passes the transport gases with the specified molecular specie content to a dual stream analyzer 64, the results of which are recorded on an upstream recorder 66 that records the concentration prior to the scrubbing process, and a downstream recorder 68 that records the concentration after the scrubbing process.

As shown in FIG. 6, the transport air may be conditioned in a transport air heat exchanger 70 and then passed into the individual mass exchangers 62a and 62b. There is a heat exchanger 72a and 72b associated with each of the diluters 62a and 62b respectively. The sample gases are diluted within this dual system in the same manner as has been previously described. Pumps 32a and 32b exhaust the unmitigated sample gases from both branches by means of drawing in the bleed air into both exhaust lines.

It is important to provide the proper dimensions and to adjust the diffusion barrier to the desired conductance. The configuration that has been described as an exemplary embodiment of the invention is particularly effective in providing predictable dilution for efficient and effective operation of the analyzer.

The diluter that has been previously described operates basically independent of the sample flow rate. The analyzer is not plugged with particulates and mist since the apparatus conditions the transport gas and selects the optimum diffusion rate. Large dilution factors can be obtained precisely with the described apparatus. The analyzer is permitted to function at optimum conditions and the effectiveness of stacks scrubbing systems is accurately determined.

Having described our invention, we now claim:

1. A gas analysis diluter comprising:
   diffuser barrier means comprising a tubular gas pervious membrane having an inlet end connected to receive a transport gas stream, a conduit surrounding said tubular membrane and having an inlet end connected to receive a sample gas stream,
   said gas pervious membrane having a large relative mass conductance to a selected molecular species of said sample gas,
   a transport gas heat exchanger for heating the sample gas to a selected temperature,
   a sample gas heat exchanger for heating the sample gas to said selected temperature.

2. A gas analysis diluter according to claim 1 wherein:
   said inlet end of said conduit is at the opposite end of said tubular member than said inlet end of said tubular member.

3. A gas analysis diluter according to claim 1 wherein:
   said transport gas and said sample gas heat exchangers, said membrane and said conduit are housed in a common cartridge housing.

4. A gas analysis diluter according to claim 1 wherein:
   said transport gas and said sample gas heat exchangers and said conduit are formed in an otherwise solid metal cartridge.

5. The diluter of claim 1 including:
   transport gas cleansing means for cleansing the transport gas prior to the admixture with a part of said sample gas.

6. The diluter of claim 1 wherein the transport gas cleansing means comprises:
   first filter means for removing particulates from the transport gas;
   oxidizer means for producing ozone which reacts with nitric oxide in the transport gas for producing nitrogen dioxide;
   second filter means downstream from the oxidizer means for removing the nitrogen dioxide, and
   third filter means downstream from second filter means for removing particulates passing the second filter means.

7. The diluter of claim 1 including:
   a pump in the sample gas line to exhaust the sample gas which does not migrate past the barrier.

8. The diluter of claim 1 wherein:
   said diluter comprises dual dilution branches,
   the first dilution branch upstream of a gas scrubbing means for diluting uncleansed sample gas, and
   the second dilution branch downstream of the gas scrubbing means for diluting cleansed sample gas.

9. The diluter of claim 4, including:
   temperature sensing means in said cartridge for sensing the temperature thereof.

* * * * *